(12) United States Patent
Blume

(10) Patent No.: US 9,211,238 B2
(45) Date of Patent: Dec. 15, 2015

(54) CARRIER SYSTEM FOR THE TRANSPORT OF ACTIVE SUBSTANCES INTO THE SKIN

(76) Inventor: Gabriele Blume, Steinau an der Strasse (DE)

(*) Notice: Subject to any disclaimer, the term of this patent is extended or adjusted under 35 U.S.C. 154(b) by 59 days.

(21) Appl. No.: 13/637,224

(22) PCT Filed: Mar. 2, 2011

(86) PCT No.: PCT/DE2011/000210
§ 371 (c)(1),
(2), (4) Date: Sep. 25, 2012

(87) PCT Pub. No.: WO2011/116738
PCT Pub. Date: Sep. 29, 2011

(65) Prior Publication Data
US 2013/0011455 A1   Jan. 10, 2013

(30) Foreign Application Priority Data
Mar. 26, 2010   (DE) .................. 10 2010 013 064

(51) Int. Cl.
| | | |
|---|---|---|
| *A61K 9/127* | (2006.01) | |
| *A61K 8/14* | (2006.01) | |
| *A61K 8/36* | (2006.01) | |
| *A61K 8/37* | (2006.01) | |
| *A61K 8/41* | (2006.01) | |
| *A61K 8/55* | (2006.01) | |
| *A61K 8/97* | (2006.01) | |
| *A61K 9/00* | (2006.01) | |
| *A61Q 19/00* | (2006.01) | |

(52) U.S. Cl.
CPC ... *A61K 8/14* (2013.01); *A61K 8/36* (2013.01); *A61K 8/37* (2013.01); *A61K 8/411* (2013.01); *A61K 8/553* (2013.01); *A61K 8/97* (2013.01); *A61K 9/0014* (2013.01); *A61K 9/127* (2013.01); *A61K 9/1272* (2013.01); *A61Q 19/00* (2013.01)

(58) Field of Classification Search
CPC ............. A61K 8/14; A61K 8/36; A61K 8/37; A61K 8/411; A61K 8/553; A61K 8/97; A61K 9/0014; A61K 9/127; A61K 9/1272; A61Q 19/00
See application file for complete search history.

(56) References Cited

U.S. PATENT DOCUMENTS

| | | | |
|---|---|---|---|
| 4,536,324 A | 8/1985 | Fujiwara et al. | |
| 4,830,857 A | 5/1989 | Handjani et al. | |
| 5,405,615 A | 4/1995 | Mathur | |
| 5,716,638 A | 2/1998 | Touitou | |
| 5,720,948 A | 2/1998 | Brucks et al. | |
| 5,830,499 A | 11/1998 | Bouwstra | |
| 6,033,710 A | 3/2000 | Miller et al. | |
| 6,419,946 B1 | 7/2002 | Sonneville et al. | |
| 2005/0158348 A1 | 7/2005 | Schwarz et al. | |
| 2005/0244488 A1 | 11/2005 | Spilburg | |
| 2007/0269379 A1 | 11/2007 | Mitragotri et al. | |

FOREIGN PATENT DOCUMENTS

| | | | |
|---|---|---|---|
| DE | 41 071 53 A1 | 9/1992 | |
| DE | 102 41 074 A1 | 11/2004 | |
| EP | 0 009 404 A2 | 4/1980 | |
| EP | 0 774 958 B1 | 1/1999 | |
| EP | 1 060 732 A2 | 12/2000 | |
| EP | 1 010 414 B1 | 4/2001 | |
| EP | 1608346 B1 | 11/2008 | |
| FR | 2 771 635 | 6/1999 | |
| WO | 96/09812 | 4/1996 | |
| WO | 00/06120 A1 | 2/2000 | |
| WO | 00/12108 A1 | 3/2000 | |
| WO | WO0012108 | * 3/2000 | ............. A61K 35/78 |
| WO | 03/047494 A2 | 6/2003 | |
| WO | 2004/022019 A1 | 3/2004 | |
| WO | 2007/123993 A1 | 11/2007 | |

OTHER PUBLICATIONS

PCT Translation of International Preliminary Report on Patentability, PCT/DE2011/000210, Oct. 11, 2012.
The International Search Report as mailed on Oct. 20, 2011 for International Application No. PCT/DE2011/000210.
Product Information IMWITOR 375, Food Grade O/W Emulsifier for Polar Oils, Sasol Germany GmbH, XP-002659490.
M.J. Choi, et al., Liposomes and Niosomes as Topical Drug Delivery Systems, Skin Pharmacol Physiol 2005; 18; pp. 209-219. Karger.
G. Blume, Liposomes = Liposomes?, SOFW-Journal 11, 2000, pp. 14-17.
C. Artmann, et al., Liposomes from Soya Phospholipids as Percutaneous Drug Carriers, Arzneimittel Forschung/Drug Research 40 (II), 12 (1990), pp. 1365-1368.
G. Cevc, Transdermal drug carriers: basic properties, optimization and transfer efficiency in the case of epicutaneously applied peptides, Journal of Controlled Release 36 (1995), pp. 3-16.
E. Touitou, Enhanced Delivery of Drugs Into and Across the Skin by Ethosomal Carriers. Drug Development Research 50 (2000), pp. 406-415.
S. Jager, Pharmacology of Selected Terpens, Pharmazeutische Zeitung Heft 22 (2006), pp. 1-10.
V.B. Patravale, Novel cosmetic delivery systems: an application update, International Journal of Cosmetic Science, 30, 2008, pp. 19-33.

* cited by examiner

*Primary Examiner* — Lezah Roberts
*Assistant Examiner* — Nannette Holloman
(74) *Attorney, Agent, or Firm* — Quarles & Brady LLP

(57) ABSTRACT

Vesicle, comprising at least the following components: —an aqueous core, which can comprise at least one cosmetic and/or at least one pharmaceutical active substance, and —a continuous membrane which surrounds the core and which is formed by at least one emulsifier, selected from the group of the food additives E 472 a to f, and at least one membrane-stabilizing single-chain lipid and/or one or more lipophilic cosmetic and/or pharmaceutical active substances.

15 Claims, 3 Drawing Sheets

Liposomes
Size >> 1000 nm

Vesicles EO
Size: 220 nm

Day 7

Encapsulation of 2.5% green tea extract

CARRIER SYSTEM FOR THE TRANSPORT OF ACTIVE SUBSTANCES INTO THE SKIN

CROSS-REFERENCE TO RELATED APPLICATIONS

This application represents the national stage entry of PCT International Application No. PCT/DE2011/000210 on Mar. 2, 2011 and claims the benefit of German Patent Application No. DE 10 2010 013 064.8 filed Mar. 26, 2010. The contents of both of these applications are hereby incorporated by reference as if set forth in their entirety herein.

The present invention relates to an improved therapeutic efficacy given by a new carrier system (lipid vesicle), that comprises both lipophilic and hydrophilic cosmetic or pharmaceutical substances and is able to transport said substances into the deeper skin layers. The present invention also relates to a preparation comprising said novel carrier system.

This kind of encapsulation of hydrophilic active substances in vesicles with a size in the sub-micron range (nm) has been well known for many years and is frequently used in particular in cosmetics and pharmacy. Vesicles which also have the ability to transport active substances into the skin are in particular the liposomes (phosphatidylcholine/lecithin) and the niosomes (non-ionic surfactant vesicles). Different compositions of these vesicles are described in the article "Liposomes and Niosomes as Topical Drug Delivery Systems" (M. J. Choi & H. I. Maibach; Skin Pharmacol. Physiol. 18 (2005) 209-219). Carrier systems that are in particular used in cosmetics are listed by Patravale and Mandawgade in a review article, (Novel cosmetic delivery systems: an application update; Int. J. Cosm. Sci. 30 (2008) 19-33).

Classical liposomes comprise a membrane-forming main component, phosphatidylcholine (PC), naturally extracted from eggs or soy lecithin but also synthetically produced. These lipids spontaneously form vesicles (multilamellar liposomes) when added into water. Depending on the composition of the phospholipids (phosphatidylcholine containing unsaturated long-chain fatty acids) and production (high pressure homogenization) small unilamellar flexible liposomes can be achieved. This kind of flexible liposomes has the ability to transport encapsulated active substances into the deeper skin layers. Artmann et al. describe small unilamellar liposomes—produced from soy lecithin (>85% PC with a high amount of unsaturated fatty acids, linoleic acid)—being able to transport encapsulated heparin of high molecular weight into the epidermis and dermis (Liposomes from Soya Phospholipids as Percutaneous Drug Carriers; Arzneimittel Forschung Drug Research 40 (1990) 1365-1368). A requirement for penetration of the liposomes into the skin is the high amount of membrane-forming phosphatidylcholine and the flexibility of the vesicle membrane, which is reflected in the article "Liposomes=Liposomes" (G. Blume; SÖFW-Journal 11 (2000) 14-17).

A further development in carrying active substances more effectively through the skin into the body (into the joints) are "transfersomes". Transfersomes differ from conventional liposomes by having edge active substances within the phospho-lipid membrane (DE 4107153). Encapsulated active substances can reach the blood even from the dermis via the lymphatic route after topical application of these ultra-flexible carriers. Thus the blood sugar level could be lowered by the application of insulin-containing transfersomes ("Transdermal Drug Carriers"; G. Cevc et al.; J. Contr. Release 36 (1995) 3-16).

A further improvement of penetration properties of small flexible liposomes can be achieved by increased addition of alcohols to the vesicle suspension (U.S. Pat. No. 5,716,638 A). The high amount of ethanol in the "ethosomes" leads to a disorganization/fluidization of skin lipids which form the skin barrier in the stratum corneum. Small flexible liposomes can reach deeper skin layers more easily due to this "disturbance" in the skin. ("Ethosomal Carriers"; E. Touitou et al.; Drug Dev. Res. 50 (2000)406-415).

Other long existing carrier systems are niosomes, which are at least formed by one non-ionic surfactant. Usually they also contain a stabilizer for the membrane (cholesterol) and a charged component (dicetyl phosphate) preventing the vesicles from aggregating. The membrane-forming component most frequently used is sorbitan mono-oleate (Span 80) but other emulsifiers are also mentioned, such as sucrose monostearate, sucrose distearate, POE (5) sorbitan trioleate and dioleyl gluconate. Some patents concerning niosomes are exemplarily listed here: U.S. Pat. No. 4,536,324 (A) describes niosomes made from PEG-10 castor oil and sorbitan trioleate; U.S. Pat. No. 4,830,857 (A) describes the production of a non-ionic surfactant and niosomes formed by this surfactant in combination with cholesterol and dicetyl phosphate; U.S. Pat. No. 5,405,615 (A) describes niosomes made from sucrose distearate and a derivative of fatty alcohols; DE Patent 69507488 describes niosomes made from PEG-2 to PEG-6 mono-hexadecyl ether, cholesterol and dicetyl phosphate; U.S. Pat. No. 5,720,948 (A) describes niosomes made from glyceryl dilaurate, cholesterol and PEG-10 stearyl ester; US Patent Application 2007/0269379 (A) describes niosomes made from N-lauryl sarcosine and sorbitan monolaurate (Span 20) and WO 2007/123993 describes niosomes made from sorbitan monostearate (Span 60), PEO sorbitan monostearate (Tween 61), cholesterol and dicetyl phosphate.

U.S. Pat. No. 5,830,499 (A) has to be particularly mentioned, which describes niosomes being able to transport active substances extremely deeply into the skin. These unilamellar vesicles consist of flexible membranes being formed of a membrane-forming non-ionic detergent and a second non-ionic, hydrophilic emulsifier. In this case even the penetration of the vesicles into the very deep skin layers was demonstrated.

Another drug carrier for dermal application is described in EP 1060732 A1: multilamellar niosomes consisting of a double-chain lipid and optionally of a single-chain lipid and a sterol. The preferred composition comprises 30-40% glyceryl distearate, 29-37% POE (10) stearyl ether and 11-14% cholesterol. The increase of the concentration of active substances in the epidermis by means of this carrier system is described.

The Spherulites® carrier system (marketed by Impag, Germany) refers to multilamellar carriers which are used in cosmetics and exhibit an optimal drug release (time release effect). Said carrier system is mentioned in FR 2771635 (A1) and comprises 30-50% of plant derived emulsifiers (esters of sugars like sucrose palmitate or sucrose distearate).

Vesicles not comprising phospholipids and being formed from an especially skin-compatible, plant derived and food-approved membrane-forming anionic emulsifier in combination with another single-chain lipid for stabilizing said vesicles have not been described before.

The problem therefore arose to find a suitable lipid composition which enables the formation of a stable and at the same time flexible carrier system which should have the ability to transport either lipophilic or hydrophilic or amphiphilic active substances into the deeper skin layers.

This problem is solved by the vesicles according to the present invention, which comprise the following components:

an aqueous core which can comprise at least one cosmetic and/or at least one pharmaceutical active substance and a continuous membrane surrounding the core, which is formed from at least one emulsifier, selected from the group of the food additives E 472 a to f, and at least one membrane-stabilizing single-chain lipid and/or one or more lipophilic active substances.

The problem is furthermore solved by a preparation comprising said vesicles.

The unilamellar vesicles according to the present invention exhibit a negative surface charge of −30 to −60 mV and preferably have a size of 80-400 nm. The vesicles are dispersed in an aqueous solution.

The vesicles according to the present invention exhibit an encapsulation efficacy which is different from that of conventional liposomes in that active substances like polyphenols (phenolic acids and flavonoids) can be included in higher concentrations into the vesicles in a stable manner.

Further advantages of the composition according to the present invention are the high stability of the composition in cosmetic and pharmaceutical formulations containing emulsifiers, the pleasant skin sensation and the fast penetration into the skin.

The membrane-forming emulsifiers used according to the present invention are suitable for consumption by humans. Anionic emulsifiers selected from the group of food additives E 472a to 472f, in particular esters of diacyl glycerides, are preferably used in the present invention. An emulsifier particularly preferred in this invention is glyceryl citrate/lactate/linoleate/oleate (Imwitor 375). The high amount of unsaturated and polyunsaturated fatty acids permits the formation of vesicles with a flexible membrane. The flexibility is a requirement for the penetration of vesicles into the skin after topical application. These emulsifiers with long alkyl chain length are characterized by a high skin compatibility and can achieve cosmetic and pharmaceutical effects (e.g. increase in skin smoothness, reduction of metalloproteases and reduction of skin impurities).

Vesicles formed by pure glyceryl citrate/lactate/linoleate/oleate in water have a highly negative surface charge of −75 mV and are instable in cosmetic formulations.

Beside the membrane-forming emulsifier, a lipophilic single-chain stabilizer is used which comprises as a hydrophobic part long-chain fatty acids (preferably oleic or eicosapentaenoic acid). Said stabilizer is necessary to achieve higher encapsulation of active substances (e.g. polyphenols) to improve the penetration properties of the vesicles and to increase the stability of the vesicles in cosmetic or pharmaceutical formulations.

For stabilizing the membrane a further food-approved emulsifier is used, such as esters of sugars of eatable fatty acids (E 473); esters of polyglycerine of eatable fatty acids (E475) and esters of propylene glycol of eatable fatty acids (E477) or a solvent, such as an ester of a long-chain fatty acid (e.g. oleic acid or eicosapentaenoic acid). These stabilizing additives with long alkyl chain length are characterized by high skin compatibility and can achieve cosmetic and pharmaceutical effects (e.g. increase in skin smoothness, reduction of metalloproteases, reduction of skin impurities, increase in skin moisture, anti-inflammatory properties).

Among the membrane stabilizing emulsifiers are sucrose oleate (Surfhope SE from Mitsubishi-Kagaku Foods Corp.), trehalose isostearate (Nomcort TQ 5 from Nisshin Oillio-group), glyceryl monooleate (Cithrol GMO from Croda), diglyceryl oleate (Nikkol DGMO-CV from Nikko Chemicals) and polyglyceryl-4-oleate (Hydriol PGMO from Hydrior).

Among the membrane-stabilizing solvents are ethyl oleate (Crodamol EO from Croda) and the ethyl ester of eicosapentaenic acid (EPA 95 EE from Equateq).

Ethyl oleate (EO) and/or Ethyl ester of eicosapentaenic acid (EE) are particularly preferred for stabilizing the membrane of the vesicles.

The amount of membrane-forming emulsifier is between 3% and 12% by weight, particularly preferably between 6% and 8% by weight, and the amount of the membrane-stabilizing single chain lipid (OE and/or EE) is between 2% and 6% by weight referring to the preparation containing vesicles. Both components form the shell of the vesicles.

The vesicles according to the invention can additionally comprise one or more lipophilic active substances embedded in the membrane of the vesicles. Such lipophilic substances are all substances which can be solved in a lipophilic medium at room temperature or under heat and have cosmetic and/or pharmaceutical effects on or in the skin.

Examples of cosmetically and/or dermatologically active lipophilic substances—preferably derived from plants—which can be used are given here: active substances for the treatment of cellulite, e.g. CLA; active substances against elastase and collagenase, e.g. unsaturated fatty acid (oleic acid or EPA); anti-inflammatory substances, e.g. EPA=eicosapentaenic acid; antioxidants, e.g. vitamin C-palmitate and tocopherol; α-lipoic acid; ceramides, e.g. certain ceramides of cosmoferm; skin calming and smoothing active substances, such as bisabolol; moisturizers, e.g. glycerol monoisostearate, sucrose polysoyate; phytosterols, such as β-sitosterol from corn oil; radical scavengers, e.g. ubiquinol derivatives such as coenzyme Q10; saponines from ginseng or licorice root and hydroxydecanoic acid; substances improving blood circulation and nutrition of the skin, such as lipophilic esters of nicotinic acid; terpenes, e.g. ursolic acid, rosmarinic acid, betulinic acid, boswellic acid and bryonolic acid (cosmetically and dermatologically relevant terpenes are listed in "Pharmazeutische Zeitung Heft 22; 2006 by Sebastian Jäger et al."); vitamins (retinol and derivatives, vitamin E and derivatives like tocotrienol or carotine and carotinoids such as lycopene, lutein or fucoxanthin, vitamin D and derivatives) and lipophilic peptides used as anti-ageing products, e.g. esters of 2-10 amino acids bound to palmitic acid.

All of these active substances are suitable to prevent or to protect the skin from ageing and/or photo-ageing (induced by UV radiation or environmental stress), to stimulate the synthesis of dermal and epidermal macromolecules or to avoid their degradation; to induce the proliferation of fibroblasts and keratinocytes, thus protecting and maintaining a healthy skin.

Pharmaceutically used vesicles according to the present invention comprise a safe and effective amount of a pharmaceutically active substance which belongs to the group of drugs against acne (e.g. isotretinoin and isolutrol), NSAIDs (non-steroidal anti-inflammatory drugs, e.g. Diclofenac), substances for healing wounds, skin diseases and eczema (e.g. corticosteroids), local anesthetics (e.g. Lidocaine), antimycotics (e.g. Terbinafin), antibiotics, substances against psoriasis (e.g. Calcipotriol), substances to stimulate hair growth (e.g. Minoxidil), substances against CVI (chronic venous insufficiency), substances against herpes infections (e.g. Aciclovir), antihistaminic substances (e.g. Dimetinden) and anticancer substances against melanoma (e.g. Diclofenac and Psoralene).

All these relevant pharmaceutical substances are effectively taken into the lower skin layers by the carrier system which leads to a higher bio-availability at the target site.

Therefore the concentration of active substances can be lowered to some extent and possible side effects can be avoided. Furthermore the encapsulation of active substances can lead to their stabilization and prevent side effects, such as skin irritation (e.g. in the case of vitamin A derivatives).

In a preferred embodiment according to the invention the weight ratio of lipophilic components in the membrane is in the range of 1:1 to 1:4 for the membrane-forming emulsifier in relation to ethyl oleate (eicosapentaenic acid ethyl ester) and/or the active substance.

The vesicles according to the present invention comprise at least one cosmetically and/or pharmaceutically active substance which is incorporated in the aqueous core or embedded in the membrane. The preparation of the vesicles according to the present invention is carried out by dispersing a solution containing the lipophilic components in an aqueous solution (dispersion vehicle), which comprises at least one hydrophilic active substance. The vesicles are then present in the aqueous dispersion and the hydrophilic active substance is present in the vesicles as well as in the aqueous dispersion vehicle. The presence of the active substance in the waterphase surrounding the vesicles enables a concentration of these components on the surface of the vesicles and permits a higher penetration of active substances into the skin.

The cosmetically and pharmaceutically active substances can be selected among others from the following substance groups:

Amino Acids, Peptides, Proteins and Enzymes:

The compositions of the present invention can comprise monomers, oligomers and polymers of amino acids as well as esters and/or physiologically accepted metallic salts of these substances.

The monomers of the amino acids can be selected from alanine, arginine, asparagine, aspartic acid, canavanine, citrulline, cysteine, glutamine, glycine, histidine, hydroxylysine, hydroxyproline, leucine, lysine, methionine, proline, serine, threonine, tyrosine and valine.

The oligomers of the amino acids are preferably selected from di-, tri-, tetra-, penta-, hexa- or pentadeca-peptides, which can be acylated and/or esterified. Numerous ones of these amino acids stimulate the synthesis of collagen and are preferably used as active substances against skin ageing.

The polymers of the amino acids are chosen from protein hydrolysates and/or proteins derived from plants or animals. Protein hydrolysates derived from animals are e.g. hydrolysates of elastin, collagen, keratin, silk and milk protein, which can also be used in the form of salts. protein hydrolysates derived from plants can be e.g. hydrolysates of soya, wheat, almond, pea, potato and rice.

In a further embodiment the enzymes might be encapsulated, selected from DNA repair enzymes (e.g. photolyase); anti-oxidatively effective enzymes (e.g superoxide dismutase (SOD), proteases (e.g. trypsin) and lipases.

Aqueous and/or Alcoholic Extracts from Plants, Fungi and Algae:

The plant extract can for example be produced by extraction from the whole plant, but also by extraction solely from flowers and/or leafs and/or seeds and/or other parts of the plant. The used extracts from algae are taken from green, brown and red algae as well from blue-green algae (cyanobacteria). The algae and fungi (in particular yeasts) used for extraction can be naturally derived, but also biotechnologically produced and can be changed in their natural form if desired. Water, alcohol or mixtures of both can be used as eluants for the plant extracts. The most preferred method for extraction according to the invention is steam distillation.

Oligonucleotides:

The composition according to the invention may comprise oligonucleotides. Mononucleotides are among others adenosine phosphate, cytidine phosphate, guanosine phosphate, uridine phosphate and thymidine phosphate, in particular CMP (cytidine-5'-monophosphate), UDP (uridine-5'-diphosphate), ATP (adenosine-5'-triphosphate) and GTP (guanosine-5'-triphosphate).

A preferred oligonucleotide according to this invention is thymidine dinucleotide (pTT), which exhibits skin tanning properties as well as DNA repairing properties.

Sugar Components:

Furthermore the compositions according to this invention can comprise mono-, oligo- or polysaccharides or their derivatives.

Preferred monosaccharides are for example glucose, fructose, galactose, arabinose, ribose, xylose, lyxose, allose, altrose, mannose, gulose, idose and talose, desoxy sugars like fucose and rhamnose or amino sugars such as glucosamine and galactosamine.

Preferred polysaccharides suitable according to the invention are formed by more than ten units of monosaccharides. Among the most preferred ones are mucopolysaccharides (such as hyaluronic acid and its derivatives, chondroitin and its derivatives, heparin and its derivatives, fucoidan and its derivatives, keratan and its derivatives) and β-glucans.

One particularly preferred complex of different sugar components is Tonsolin (Gova Group), which contains mannose, glucose, β-glucan and hyaluronic acid and induces a fast and safe tanning of the skin.

Hydroxy and Keto Carboxylic Acids and Their Salts:

Further preferred hydrophilic components are α-hydroxy carboxylic acids, α-keto carboxylic acids or β-hydroxy carboxylic acids and their esters, lactones or salts. The following substances belong to this group: glycolic acid, lactic acid, tartaric acid, citric acid, 2-hydroxy hexadecanoic acid, mandelic acid, malic acid, glucaric acid, galactaric acid, mannaric acid, gluconic acid, pyruvic acid, salicylic acid, glucuronic acid and galacturonic acid.

Vitamins:

In another embodiment the compositions according to the invention can comprise a water-soluble vitamin selected from the vitamin groups B and C and the esters of the aforementioned substances.

The following vitamins among others belong to the group of vitamin B or to the vitamin B-complex: vitamin $B_1$, (thiamine), thiamine hydrochloride, vitamin $B_2$ (riboflavin), riboflavin and its derivatives, vitamin $B_3$ (niacin and niacinamide), vitamin $B_6$-group (pyridoxine, pyridoxamine and pyridoxal), vitamin $B_7$ (biotin)

Vitamin C (ascorbic acid) is preferably used in its stabilized derivatives: ascorbyl acetate, magnesium ascorbyl phosphate, sodium ascorbyl phosphate, sodium and magnesium ascorbate, disodium ascorbyl phosphate and -sulfate, potassium ascorbyl tocopheryl phosphate and ascorbyl glucoside.

Polyphenols:

Polyphenols are aromatic compounds comprising two or more hydroxyl-groups directly attached to an aromatic ring and belonging to the category of secondary plant metabolites. Natural polyphenols can be found in plants as biologically active components, such as dyes (flavonoids, anthocyanins), flavors and tannins. Phenolic acids and flavonoids belong to the category of polyphenols and are encapsulated in the vesicles due to their cosmetic and/or pharmaceutical effects (e.g. anti-oxidative, anti-inflammatory, antibacterial and antiviral properties).

The phenolic acids usable according to this invention are e.g. gallic acid, vanillic acid, usnic acid, ferulic acid, ellagic acid and caffeic acid.

The flavonoids and/or their glycosylated derivatives usable according to the present invention comprise among others: flavons (luteolin, apigenin), flavonols (baicalin, quercetin, rutin, camphor, myricetin), flavanols (catechin, gallocatechin, epicatechin, epigallocatechingallate, resveratol, silymarin, theaflavin), flavanons (aspalathin, hesperetin, naringenin), flavanonols (taxifolin), isoflavons (genistein, daidzein, licoricidin) and anthocyanidins or anthocyans (natural dyes).

A particularly preferable combination for encapsulation into the vesicles is univestin (unigen), consisting mainly of baicalin and catechin, which is characterized by a high antioxidative potential and good anti-inflammatory properties.

Tanning:

Active substances being able to induce skin pigmentation can be incorporated into vesicles according to the invention, such as. erythrulose; Unipertan Veg (mixture of acetyltyrosin, riboflavin and hydrolysed proteins from plants marketed by Induchem); Tonsolin (mixture of sugars by Goya), dinucleotid pTT and the melanin-stimulating peptide (like e.g. α-melanotropin).

Skin Lightener:

Another preferred embodiment of the composition according to the invention comprises an active substance for skin brightening and whitening, such as ascorbic acid or its esters (sodium ascorbyl phosphate, magnesium ascorbyl phosphate) or hydroxy tyrosol (Cayoma Olive from Qenax).

Antioxidants:

The compositions according to the invention can further comprise antioxidants, such as imidazols (urocaninic acid) and their derivatives; peptides (e.g. D,L-carnosin, D-carnosin, L-carnosin); acids and their derivatives (chlorogenic acid, huminic acid, gallic acid, rutinic acid and ferulic acid); vitamins (vitamin C and its derivatives, e.g. magnesium ascobyl phosphate); enzymes (catalase and superoxide dismutase); zinc and its derivatives ($ZnO$, $ZnSO_4$), selenium and its derivatives (selenium methionine), stilbenes and their derivatives (e.g. resveratol)

All of these active substances are used to inhibit or to prevent skin ageing and/or photo-ageing (induced by UV radiation or environmental stress), to stimulate the synthesis of dermal and epidermal macromolecules or to prevent their degradation, to induce the proliferation of fibroblasts and keratinocytes, thus protecting and maintaining healthy skin.

In a preferred embodiment according to the present invention the ratio in weight of the lipophilic components of the membrane is between 5% and 15% by weight (Imwitor: stabilizer: active substance), in particular preferably between 8% and 10% by weight and for the used hydrophilic active substance between 0.1% and 20% in relation to the complete composition. The concentration of the hydrophilic active substance can vary and is strongly dependent on the solubility of the respective substance.

The compositions according to the invention can further comprise at least one stabilizer, which is preferably a water-soluble alcohol. This stabilizer/solvent is preferably used in concentrations between 10% and 20% by weight in relation to the entire composition. Depending on the pharmaceutical form, suitable alcohols are monovalent alcohols, such as. ethanol, propanol, isopropanol or natural phenyl ethyl alcohol. Further suitable are water-soluble polyols, such as. water-soluble diols, triols and alcohols of higher valency. Suitable diols are $C_2$ through $C_{10}$-diols, preferably 1,2-propylene glycol, 1,2-butylene glycol, 1,3-butylene glycol and 1,4-butylene glycol, 1,2-pentylene glycol, 1,6-hexandiol and 1,2 octandiol. Further preferably suitable are glycerin and in particular diglycerin and triglycerin, 1,2,6-hexantriol and dipropylene glycol. For the production of the vesicles according to the invention ethanol, phenylethyl alcohol or 1,2 pentylene glycol (Hydrolite 5 from Symrise) are preferably used in concentrations of 10% to 30% by weight, particularly preferably 15%-20% by weight in relation to the entire composition. Thus no additional preservatives are necessary (conventional preservation) and therefore the composition according to the invention can be declared free from preservatives.

The aqueous composition containing the vesicles can itself be used as a cosmetic or pharmaceutical preparation depending on the added active substance contained therein. Moreover the aqueous composition containing the vesicles can be worked into the water phase of a further formulation, such as an emulsion, lotion, cream or different forms of gels, or can even be diluted and be used with an additional thickener as a spray formulation.

The described invention also comprises the use of the vesicles in cosmetically, dermatologically and pharmaceutically relevant aqueous formulations (e.g. spray formulations, different gels, lotions and creams) as well as their application for the treatment, protection and care of skin, hair, nails and lips.

In the following the method for producing a composition according to the invention is demonstrated by means of several application examples and illustrations, which shall not be understood as limiting.

EXAMPLE 1

Encapsulation of the Hydrophilic Active Substance "Green Tea Extract" (KOSME Green Tea Extract)

All formulations comprise by weight: 10% lipid, 16% ethanol, 2.5% green tea extract and 71.5% water.

First a stock solution was prepared by adding 8 g ethanol+ 2.5 g green tea extract+71.5 g water.

Liposomes:

10 g phospholipids (Phospholipon 85 G from Lipoid) were dissolved in 8 g ethanol. This solution was added to 82 g of the green tea stock solution under homogenization. After this the dispersion was homogenized by high pressure for 5 minutes at 200 bar.

The size of the vesicles was 211 nm and PDI=0.409 (an extremely inhomogeneous distribution pattern); pH=6.18

Vesicles EO (vesicles comprising ethyl oleate):

7 g Imwitor 375+3 g Crodamol EO were dissolved in 8 g ethanol. This solution was added to 82 g of the green tea stock solution under homogenization. After this the dispersion was homogenized by high pressure (5 minutes at 200 bar).

The size of the vesicles was 122 nm and PDI=0.091 (a very homogeneous distribution pattern); pH=6.1

Figure 1:
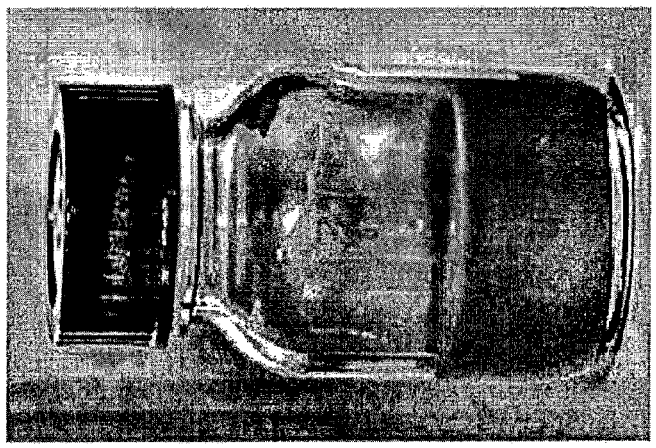
FIG. 1 illustrates green tea extract encapsulated in liposomes and vesicles EO, one week after they were produced.
Figure 1:
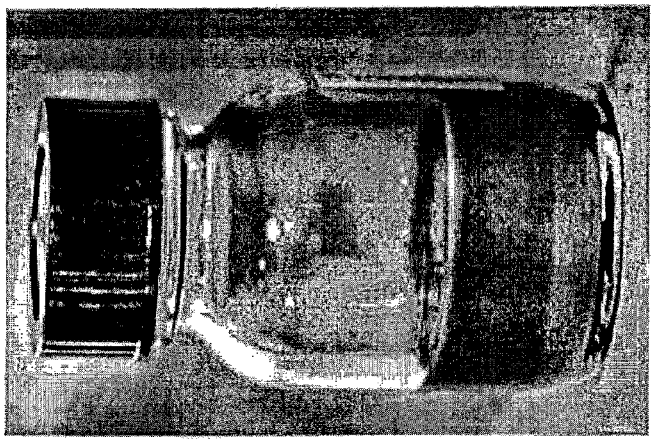

After one week a major sedimentation of green tea was observed in the liposomal preparation whereas the vesicles EO kept stable as can be seen in FIG. 1.

EXAMPLE 2

Encapsulation of the Amphiphilic Active Substance "Ferulic Acid"

Liposomes:

First 1 g ferulic acid (GfN) was dissolved in 16 g ethanol and then 10 g phopsholipids (Phospholipon 85 G from Lipoid) were added and dissolved, too. This solution was added to 73 g phosphate buffer (pH 7.2) under homogenization. Afterwards the dispersion was homogenized by high pressure for 5 minutes at 200 bar.

The size of the vesicles was 85 nm and PDI=0.386 (a very inhomogeneous distribution pattern); pH=5.7.

After two weeks storage a streaking could be observed.

Pure Imwitor:

First 1 g ferulic acid (GfN) was dissolved in 16 g ethanol and then 10 g Imwitor 375 were added and solubilized. This solution was added to 73 g water under homogenization. Afterwards the dispersion was homogenized by high pressure (5 minutes at 200 bar).

The size of the vesicles was 174 nm and PDI=0.213 (homogeneous distribution pattern); pH=5.3.

Vesicles EO:

First 1 g ferulic acid (GfN) was dissolved in 16 g ethanol and then 7 g Imwitor 375+3 g Crodamol EO were added and solubilized. This solution was added to 73 g water under homogenization. Afterwards the dispersion was homogenized by high pressure for 5 minutes at 200 bar.

The size of the vesicles was 124 nm and PDI=0.068 (very homogeneous distribution pattern); pH=5.6.

Vesicles EE (containing the ethyl ester of eicosapentaenic acid):

First 1 g ferulic acid (GfN) was dissolved in 16 g ethanol and then 7 g Imwitor 375+2 g Crodamol EO+1 g EPA 95 EE were added and solubilized. This solution was added to 73 g water under homogenization. Afterwards the dispersion was homogenized by high pressure for 5 minutes at 200 bar.

The size of the vesicles was 124 nm and PDI=0.060 (very homogeneous distribution pattern); pH=5.67.

The anti-oxidative potential (AP) of all described formulations was determined in vitro. In this method the formulations were incubated with a test radical (DPPH) and afterwards the reduction of these radicals over the time was measured by ESR (electron spin resonance spectroscopy). AP=amount of free radicals/mg of tested substance*minute.

| | |
|---|---|
| 1% ferulic acid (EtOH/water): | AP = 723 |
| 1% ferulic acid in liposomes: | AP = 2.220 |
| 1% ferulic acid Imwitor vesicles: | AP = 980 |
| 1% ferulic acid vesicles EO: | AP = 2.073 |
| 1% ferulic acid vesicles EE: | AP = 2.017 |

Figure 2:
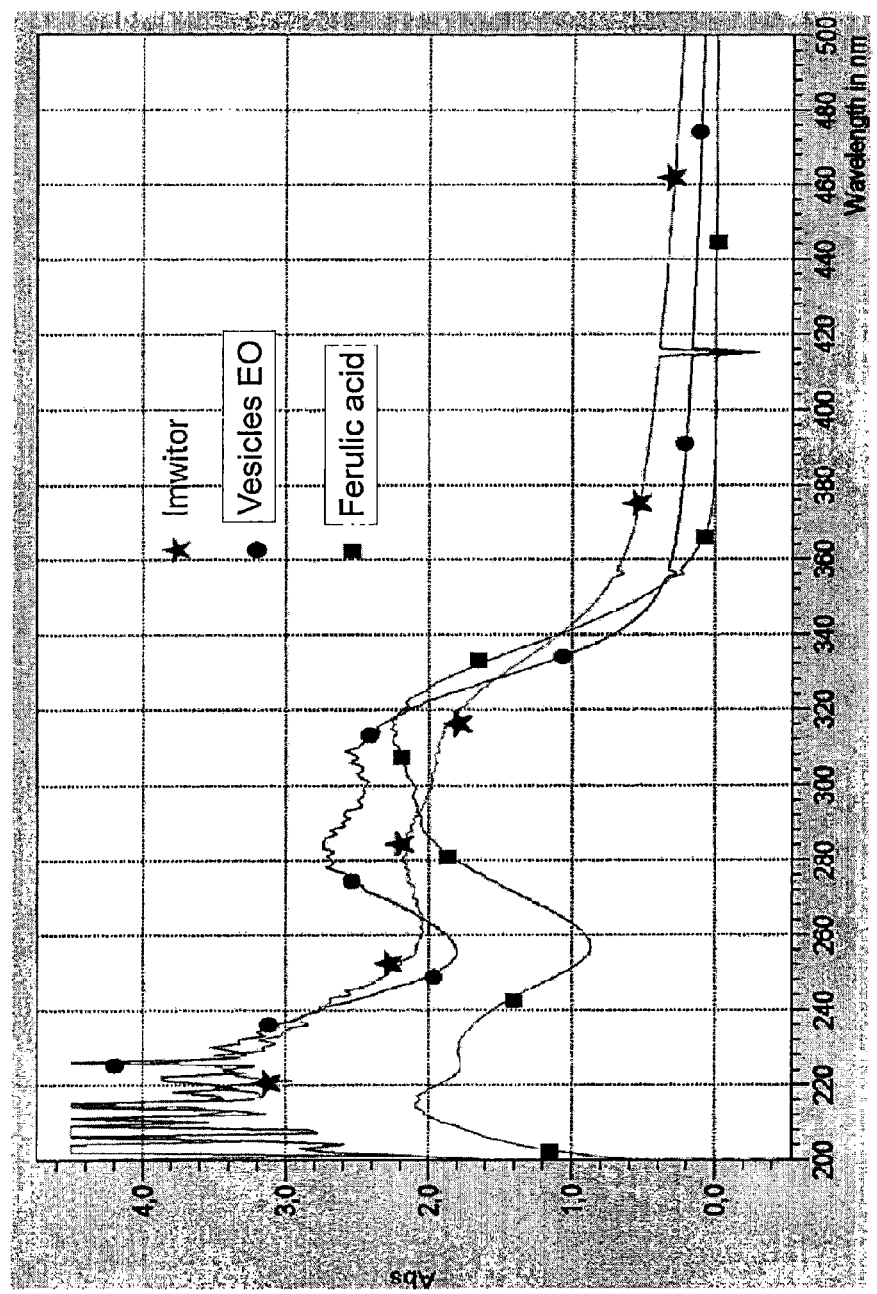
FIG. 2 illustrates UV photometric spectra of ferulic acid, both in its pure form and encapsulated in vesicles made of Imwitor.

It becomes clear, that the vesicles formed by pure Imwitor only show a minor activating effect on the ferulic acid (factor 1.36) whereas the other stable membranes can increase the AP of ferulic acid by the factor 3.1 for liposomes and 2.8 for vesicles EO/EE, respectively. UV-photometric spectra show the changes in the maximum of absorption of ferulic acid when incorporated into vesicles made of pure Imwitor (FIG. 2)

Figure 3:
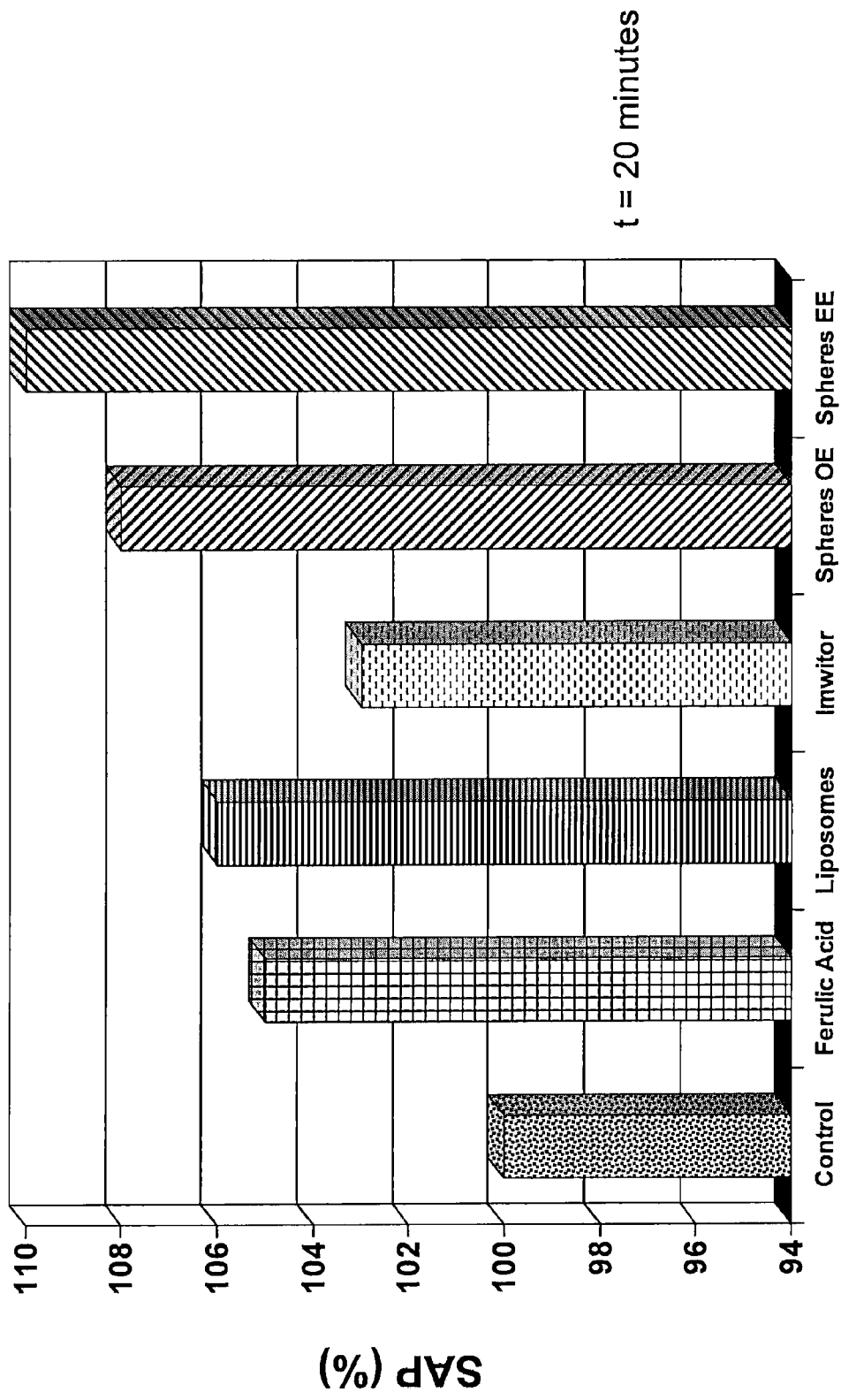
FIG. 3 illustrates the skin anti-oxidative potential of ferulic acid, both in its pure form and encapsulated in different carrier systems.

The penetration ability of ferulic acid with the help of carrier systems into the skin was determined by ESR spectroscopy. The skin has a natural anti-oxidative protection due to enzymatic and non-enzymatic active substances present in the epidermis. This anti-oxidative potential (SAP) of the skin can be measured by ESR spectroscopy by incubating the epidermis with test radicals and observing the reduction of the radicals by ESR (equivalent to 100%). Topically applied antioxidants which can penetrate into the skin are then able to increase the SAP. Only the vesicles EE and EO show a significant increase of the SAP (FIG. 3).

EXAMPLE 3

Encapsulation of the Lipophilic Active Substance "Diclofenac" Spheres EE:

First 2 g Diclofenac were dissolved in 16 g ethanol and then 7 g Imwitor 375+1 g EPA 95 EE were added and solubilized. This solution was added to 73 g water under homogenization. Afterwards the dispersion was homogenized by high pressure for 5 minutes at 200 bar.

The size of the vesicles was 135 nm and PDI=0.096 (very homogeneous distribution pattern).

EXAMPLE 4

Stability of Vesicles in a Cosmetic Formulation

The integrity of the vesicle membrane in cosmetic formulations is determined by ESR spectroscopy. A label which is detectable by ESR is incorporated into the vesicle membrane. This label is different in its ESR-signals when it is embedded in the membrane or freely dispersed in the formulation.

| | Stability in % | | |
|---|---|---|---|
| | t = 0 | t = 24 h | t = 48 h |
| Liposomes | 95 | 90 | 90 |
| Imwitor vesicle | 90 | 60 | 40 |
| Vesicles EO | 90 | 80 | 80 |

Formulation: water, hydrogenated jojoba oil, steareth-2; PPG-15 stearyl ether; glycerin; canola oil; steareth-21; shea butter; dicaprylyl ether; cyclomethicone; xanthan gum

The invention claimed is:

1. Vesicles comprising:
   a. an aqueous core comprising at least one cosmetic and at least one pharmaceutical active substance, and
   b. a flexible, continuous membrane surrounding the aqueous core, the flexible, continuous membrane comprising
      i. at least one membrane-forming emulsifier; wherein the emulsifier is glyceryl citrate/lactate/linoleate/oleate;
      ii. at least one membrane-stabilizing single-chain lipid;
      iii. one or more lipophilic cosmetic; and
      iv. at least one-pharmaceutical active substance.

2. Vesicles according to claim 1, characterized in that the vesicles are unilamellar, exhibiting a negative surface potential and a vesicle size from 80 nm to 400 nm.

3. Vesicles according to claim 1, characterized in that the membrane-stabilizing single-chain lipid is an ethyl ester of oleic acid and/or an ethyl ester of eicosapentaenic acid.

4. Vesicles according to claim 3, characterized in that the ratio in weight of the emulsifier to the membrane stabilizer and/or the lipophilic active substance is 1:1 to 4:1.

5. Preparation comprising the vesicles according to claim 1, characterized in that the dispersion vehicle of the preparation is aqueous, wherein the aqueous dispersion vehicle and the aqueous core of the vesicles exhibit the same composition.

6. Preparation according to claim 5 characterized in that it further comprises at least one hydrophilic stabilizer.

7. Preparation according to claim 5 wherein the preparation is a human or animal therapeutic.

8. Preparation according to claim 5 wherein the preparation is a cosmetic or non-therapeutic dermatological preparation.

9. Vesicles according to claim 2, characterized in that the membrane-stabilizing single-chain lipid is an ethyl ester of oleic acid and/or an ethyl ester of eicosapentaenic acid.

10. Preparation comprising the vesicles according to claim 2, characterized in that the dispersion vehicle of the preparation is aqueous, wherein the aqueous dispersion vehicle and the aqueous core of the vesicles exhibit the same composition.

11. Preparation comprising the vesicles according to claim 3, characterized in that the dispersion vehicle of the preparation is aqueous, wherein the aqueous dispersion vehicle and the aqueous core of the vesicles exhibit the same composition.

12. Preparation comprising the vesicles according to claim 4, characterized in that the dispersion vehicle of the preparation is aqueous, wherein the aqueous dispersion vehicle and the aqueous core of the vesicles exhibit the same composition.

13. Preparation according to claim 6 wherein the preparation is a human or animal therapeutic.

14. Preparation according to claim 6 wherein the preparation is a cosmetic or non-therapeutic dermatological preparation.

15. Preparation according to claim 7 wherein the preparation is a cosmetic or non-therapeutic dermatological preparation.

* * * * *